US00PP26663P2

(12) United States Plant Patent
Nishikawa

(10) Patent No.: US PP26,663 P2
(45) Date of Patent: Apr. 26, 2016

(54) ***CALENDULA* PLANT NAMED '20124-30D'**

(50) Latin Name: *Calendula officinalis*
Varietal Denomination: 20124-30D

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 100 days.

(21) Appl. No.: 14/120,524

(22) Filed: May 29, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — June Hwu
(74) *Attorney, Agent, or Firm* — Penny J. Aguirre

(57) ABSTRACT

A new cultivar of *Calendula* plant, '20124-30D', that is characterized by its strong, compact, creeping plant habit, its double flowers that are a bright yellow-orange in color, its long flowering time; blooming for 9 months from spring into winter in Noordwijkerhout, The Netherlands, its very high tolerance to powdery mildew, and its very high tolerance to heat and cold, withstanding temperatures below −20° C. in the winter and its ability to be readily propagated by stem cuttings.

2 Drawing Sheets

Botanical classification: *Calendula officinalis.*
Variety denomination: '20124-30D'.

CROSS REFERENCE TO RELATED APPLICATIONS

This application is co-pending with U.S. Plant Patent Applications filed for plants derived from the same breeding program that are entitled *Calendula* Plant Named '20124-R' (U.S. Plant patent application Ser. No. 14/120,527) and *Calendula* Plant Named '20123-5D' (U.S. Plant patent application Ser. No. 14/120,525).

BACKGROUND OF THE INVENTION

The present invention relates to a new and distinct cultivar of *Calendula* plant, botanically known as *Calendula officinalis* '20124-30D' and will be referred to hereinafter by its cultivar name, '20124-30D'. The new cultivar of *Calendula* is an herbaceous perennial grown for container and landscape use.

The new cultivar was derived from a controlled breeding program conducted by the Inventor in Katsuta-Gun, Okayama-Pref., Japan. The overall purpose of the breeding program was to develop new cultivars of vegetatively propagated *Calendula* plants with low-growing and well-spreading growth habits combined with long flowering periods and a unique range of flower colors.

'20124-30D' was selected in the Inventor's trial garden in 2012 as a single unique plant from amongst the seedlings derived from self-crossing an unnamed plant from the Inventor's breeding program, ref. code 20122-33D, in 2012.

Asexual propagation of the new cultivar was first accomplished by softwood stem cuttings in summer of 2012 by the Inventor in Katsuta-Gun, Okayama-Pref., Japan. Asexual propagation by softwood stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish '20124-30D' as a unique cultivar of *Calendula.*

1. '20124-30D' exhibits a strong, compact, creeping plant habit.
2. '20124-30D' exhibits double flowers that are a bright yellow-orange in color.
3. '20124-30D' exhibits a long flowering time; blooming for 9 months from spring into winter in Noordwijkerhout, The Netherlands.
4. '20124-30D' exhibits very high tolerance to powdery mildew.
5. '20124-30D' exhibits very high tolerance to heat and cold, withstanding temperatures below −20° C. in the winter.
6. '20124-30D' is readily propagated by stem cuttings.

'20124-30D' can best be compared to plants of the *Calendula* seed strain 'Alice'. 'Alice' differs from '20124-30D' in having flowers that are larger in size, in having a shorter four month long blooming period, in being poorly branched, in being susceptible to powdery mildew, heat, and cold, and in being propagated by seed. '20124-30D' can also be compared to the co-pending *Calendula* cultivars '20124-R' and '20123-5D'. '20124-R' differs from '20124-30D' in having flowers that are yellow in color. '20123-5D' differs from '20124-30D' in having flowers that are a blend of pale yellow to light peach in color. There are no cultivars of *Calendula officinalis* that are vegetatively propagated known to the Inventor. The Inventor has no records on the characteristics of the parent plant.

BRIEF DESCRIPTION OF THE DRAWINGS

The accompanying colored photographs illustrate the overall appearance and distinct characteristics of the new *Calen-*

*dula*. The plant in the photograph is four months in age as grown outdoors in a 20-cm container in Noordwijkerhout, The Netherlands.

Figure 1:
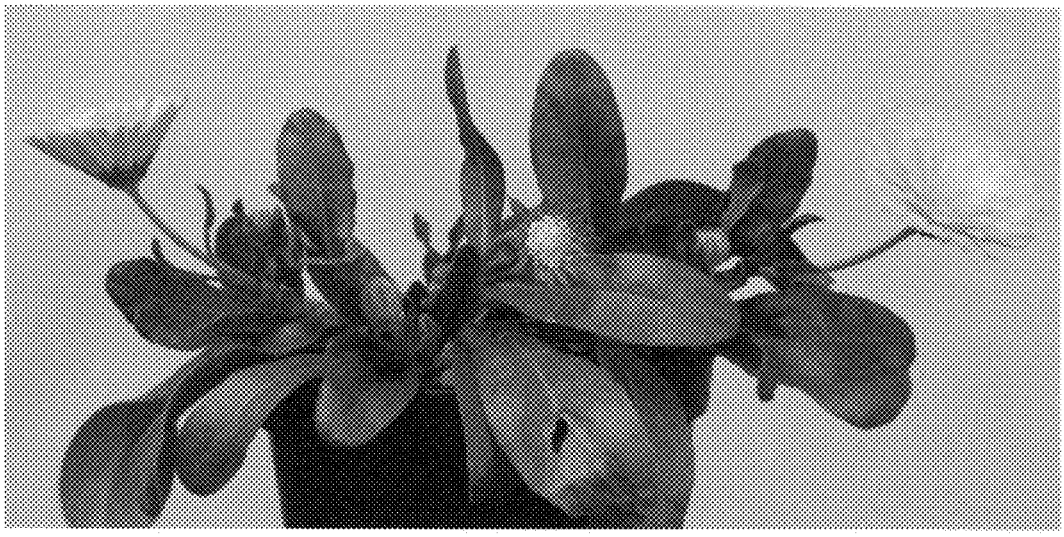

The photograph in FIG. 1 provides a side view of the plant habit of '20124-30D' in bloom.

Figure 2:
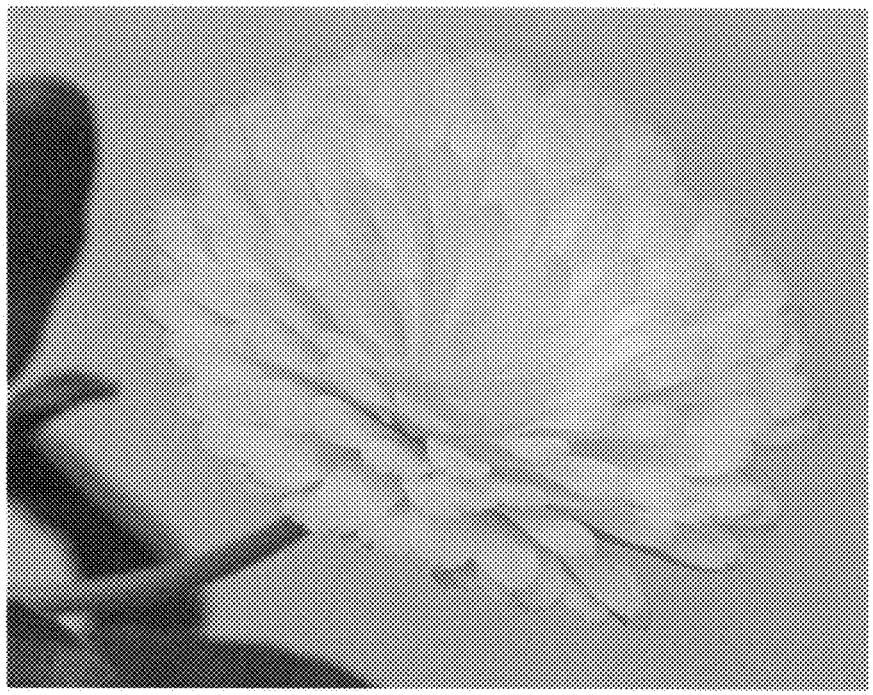

The photograph in FIG. 2 provides a close-up view of a flower of '20124-30D'.

Figure 3:
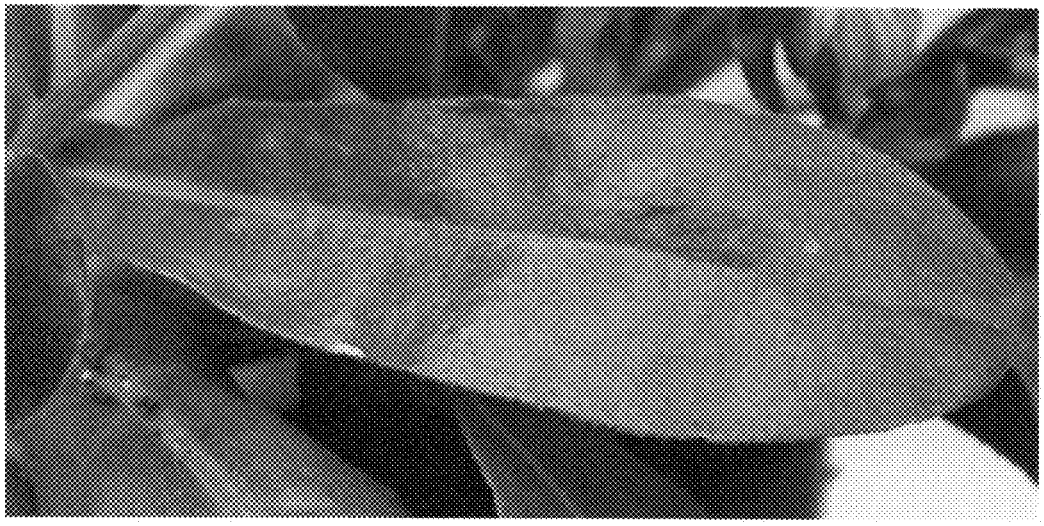

The photograph in FIG. 3 provides a close-up view of the foliage of '20124-30D'.

The colors in the photographs may differ slightly from the color values cited in the detailed botanical description, which accurately describe the colors of the new *Calendula*.

DETAILED BOTANICAL DESCRIPTION

The following is a detailed description of four month-old plants of the new cultivar as grown outdoors in 20-cm containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—An average of nine-months from spring into winter in Noordwijkerhout, The Netherlands.

*Plant type.*—Herbaceous perennial.

*Plant habit.*—Compact and creeping.

*Height and spread.*—Reaches about 9.5 cm in height and 23.2 cm in diameter.

*Cold hardiness.*—Observed to be hardy to U.S.D.A. Zone 7.

*Diseases.*—Has been shown to be tolerant of powdery mildew.

*Root description.*—Fine and fibrous roots.

*Propagation.*—Softwood stem cuttings.

*Growth habit.*—Vigorous.

Stem description:

*Shape.*—Rounded.

*Stem color.*—143C.

*Stem size.*—An average of 5.8 cm in length and 0.5 cm in diameter.

*Stem strength.*—Strong.

*Stem aspect.*—Stems grow in a moderate angle of 70° from the base (0°=horizontal) to the main stem.

*Stem surface.*—Moderately glossy, sparsely covered with very short soft hairs; 0.07 cm in length and NN155D in color.

*Stem number.*—5 lateral branches.

*Internode length.*—Average of 1.1 cm in length.

*Branching.*—Branches grow from base.

Foliage description:

*Leaf shape.*—Narrow oblanceolate.

*Leaf division.*—Simple.

*Leaf base.*—Truncate, decurrent.

*Leaf apex.*—Obtuse.

*Leaf venation.*—Pinnate, color: upper surface; 146D, lower surface; 144A.

*Leaf margins.*—Entire, moderately covered with very short strigose hairs; average length of 0.04 cm and NN155D in color.

*Leaf attachment.*—Sessile.

*Leaf arrangement.*—Alternate.

*Leaf size.*—Average of 11.1 cm in length and 3.2 cm in width.

*Leaf color.*—Young upper surface; N137A, young lower surface; N137D, mature upper surface; N137A, mature lower surface; 147B.

*Leaf surface.*—Upper and lower surfaces are moderately rough to the touch and moderately covered with very short strigose hairs 0.03 cm in length and NN155D in color, upper surface is moderately glossy and lower surface is very slightly glossy and moderately rough to the touch.

*Leaf fragrance.*—None.

*Petioles.*—No petioles present, leaves are decurrent.

Inflorescence description:

*Inflorescence type.*—Terminal capitulum consisting of ray florets only.

*Inflorescence number.*—An average of 12 per plant.

*Flower number.*—Average of 1 per lateral stem.

*Flower fragrance.*—No fragrance.

*Flower aspect.*—Straight on top of stem.

*Flower longevity.*—A few weeks.

*Flower size.*—Average of 1.8 cm in height and 6.2 cm in diameter, disc diameter is 0.4 cm.

*Flower buds.*—Average of 1 per lateral stem, broad ovate in shape, average of 1.3 cm in length and 1.1 cm in diameter, color; 138A to 138B, apex is 23A to 23B.

*Receptacle.*—Flattened rhomboidal in shape, 0.3 cm in height and 0.6 cm in diameter, a blend of 144A and 137B in color.

*Peduncle.*—4.1 cm in length and 0.2 cm in diameter, terminal peduncle is straight on top of stem, other peduncles at an average angle of 30° to the stem, moderate strength, color is 143C, moderately covered with short soft hairs; average of 0.07 cm in length and NN155D in color.

*Involucral bracts* (*phyllaries*).—Average of 28 per inflorescence, arranged in 2 rows, lanceolate in shape, narrowly acute apex, cuneate base, margin entire, 1 cm in length, 0.2 cm in width, upper surface is glossy and glabrous, lower surface is matte and densely covered with very short pubescence; average length is 0.05 cm and NN155C in color, color: upper surface 137D, lower surface 137C.

Ray florets:

*Number.*—Average of 140.

*Arrangement.*—Rotate, 7 whorls.

*Shape.*—Oblanceolate.

*Aspect.*—Slightly upright at the base, held in an average angle of 30°, whole ray floret near horizontal.

*Size.*—Average of 2.9 cm in length and 0.55 cm in width.

*Ray floret apex.*—Praemorse.

*Ray floret base.*—Narrow cuneate.

*Ray floret margins.*—Entire.

*Ray floret surface.*—Both sides glabrous and matte, upper surface is velvety.

*Ray floret color.*—Opening upper surface; 12C to 12D, tip is 23A, base is 14A to 14B, opening lower surface; 21A, when fully open upper surface; 13B, tip is 23A, base 12A, when fully open lower surface; 13A, tip is 24A to 25A.

*Disk florets.*—Glabrous and glossy surfaces, spirally placed on disc average of 5 disc florets per inflorescence, shape is tubular, upper $1/6^{th}$ of disk florets free, tip is acute, fused into tube, entire margin, average of 0.6 cm in length and 0.2 cm in width, color of upper and lower surfaces when opening and fully opened is 9B with mid-section 9C and base 150D.

Reproductive organs (ray florets pistillate, disc florets perfect):

*Gynoecium.*—1 pistil per ray floret, 0.4 cm in length, stigma unequal decurrent and 17C in color, style is 0.2 cm in length and 12A in color, ovary 150D in color.

*Androecium.*—5 stamens, filament length is 0.2 cm and 1C in color, anther shape is linear, 0.2 cm in length and 22A in color, pollen amount is very low and too low to be measured by RHS-CC.

*Fruit and seed.*—No fruits or seeds observed to date.

It is claimed:

1. A new and distinct variety of *Calendula* plant named '20124-30D' as described and illustrated herein.

* * * * *